(12) United States Patent
Zeevaart

(10) Patent No.: US 12,327,649 B2
(45) Date of Patent: Jun. 10, 2025

(54) PRODUCTION OF RADIOISOTOPES

(71) Applicant: The South African Nuclear Energy Corporation SOC Limited, North West Province (ZA)

(72) Inventor: Jan Rijn Zeevaart, Pretoria (ZA)

(73) Assignee: The South African Nuclear Energy Corporation SOC Limited, North West Province (ZA)

( * ) Notice: Subject to any disclaimer, the term of this patent is extended or adjusted under 35 U.S.C. 154(b) by 1018 days.

(21) Appl. No.: 16/623,333

(22) PCT Filed: Jun. 29, 2018

(86) PCT No.: PCT/IB2018/054858
§ 371 (c)(1),
(2) Date: Dec. 16, 2019

(87) PCT Pub. No.: WO2019/003202
PCT Pub. Date: Jan. 3, 2019

(65) Prior Publication Data
US 2020/0312476 A1     Oct. 1, 2020

(30) Foreign Application Priority Data

Jun. 29, 2017   (ZA) .................. 2017/04408

(51) Int. Cl.
*G21G 1/00*      (2006.01)
*A61K 51/00*      (2006.01)
(Continued)

(52) U.S. Cl.
CPC ............. *G21G 1/12* (2013.01); *A61K 51/00* (2013.01); *A61N 5/1001* (2013.01);
(Continued)

(58) Field of Classification Search
None
See application file for complete search history.

(56) References Cited

U.S. PATENT DOCUMENTS 5,784,423 A * 7/1998 Lidsky ................. G21G 1/10
376/156
5,949,836 A * 9/1999 Lidsky ................. G21G 1/12
376/156
(Continued)

FOREIGN PATENT DOCUMENTS

CN      116887889 A * 10/2023 ......... A61F 9/00781
DE   102010030713 A1 * 8/2011 ............. H01J 35/08
(Continued)

OTHER PUBLICATIONS

Van Dorp, Jan Willem J., et al. "Towards the production of carrier-free 99Mo by neutron activation of 98Mo in molybdenum hexacarbonyl-Szilard-Chalmers enrichment." Applied Radiation and Isotopes 140 (2018): 138-145. (Year: 2018).*
(Continued)

*Primary Examiner* — Lily C Garner
(74) *Attorney, Agent, or Firm* — Edwin S. Flores; Daniel J. Chalker; Chalker Flores, LLP

(57) ABSTRACT

A method of obtaining, from a target compound, a radioisotope of a target element comprised in the target compound includes irradiating the target compound with high energy photon irradiation (gamma irradiation). Thereby the target element radioisotope is formed. The method is performed such that the target element radioisotope is of different oxidation state than the target element, and is comprised in a target element radioisotope compound that is separable from the target compound by a physical and/or chemical separation method.

9 Claims, 1 Drawing Sheet

Figure 1:
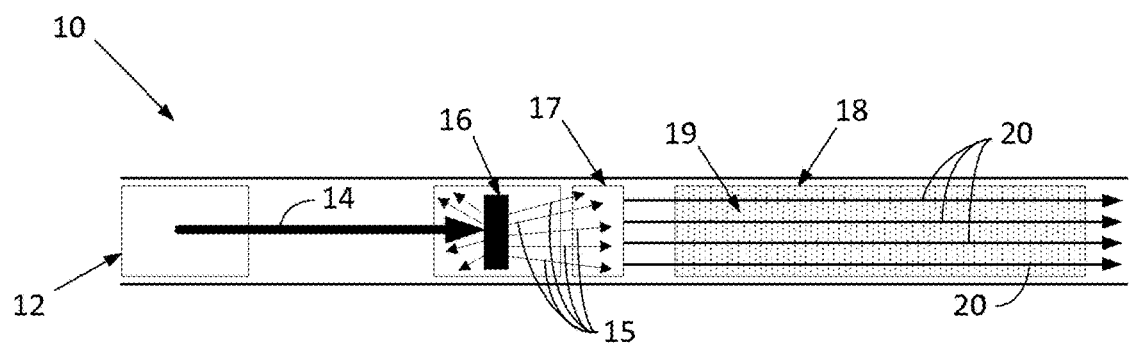

(51) Int. Cl.
  *A61N 5/10* (2006.01)
  *G21G 1/12* (2006.01)
(52) U.S. Cl.
  CPC ............. *A61N 2005/1019* (2013.01); *A61N 2005/1089* (2013.01); *G21G 2001/0036* (2013.01)

(56) References Cited

U.S. PATENT DOCUMENTS

| | | | | |
|---|---|---|---|---|
| 7,486,771 | B2 * | 2/2009 | Stichelbaut | A61L 2/082 378/69 |
| 9,047,998 | B2 * | 6/2015 | Jansen | G21G 1/06 |
| 9,269,467 | B2 * | 2/2016 | Stevenson | G21G 1/10 |
| 9,336,916 | B2 * | 5/2016 | Stevenson | G21G 1/10 |
| 9,837,176 | B2 * | 12/2017 | Diamond | G21G 1/001 |
| 9,889,424 | B2 * | 2/2018 | Tadokoro | B01J 19/0013 |
| 11,145,430 | B2 * | 10/2021 | Campanella | H05H 6/00 |
| 2005/0069076 | A1 * | 3/2005 | Bricault | G21G 1/10 376/190 |
| 2011/0280357 | A1 * | 11/2011 | Stevenson | G21G 1/10 376/195 |
| 2012/0281799 | A1 * | 11/2012 | Wells | G21G 1/12 376/157 |
| 2012/0307953 | A1 * | 12/2012 | Stevenson | G21G 1/10 376/190 |
| 2014/0348284 | A1 * | 11/2014 | Diamond | G21G 1/06 376/202 |
| 2017/0323696 | A1 * | 11/2017 | Kani | G21G 1/10 |

FOREIGN PATENT DOCUMENTS

| | | | | |
|---|---|---|---|---|
| EP | 3522177 | B1 * | 9/2020 | ............... A61N 5/10 |
| WO | WO-1992003179 | A1 * | 3/1992 | |
| WO | WO-9222190 | A1 * | 12/1992 | ............... H05H 7/18 |
| WO | WO-9709724 | A1 * | 3/1997 | ............... G21G 1/10 |
| WO | 2008/081480 | A1 | 7/2008 | |
| WO | WO-2024057756 | A1 * | 3/2024 | |

OTHER PUBLICATIONS

Pugachev, G. D., et al. "Design of the target for 99Mo production in the electron linear accelerator." Voprosy Atomnoj Nauki i Tekhniki. Yaderno-Fizicheskie Issledovaniya (1999): 95-96. (Year: 1999).*
Le, Van So. "Generator development: up-to-date recovery technologies for increasing the effectiveness of utilisation." Science and Technology of Nuclear Installations 2014 (2014). (Year: 2014).*
Rusev, G., et al. "Systematics of magnetic dipole strength in the stable even-mass Mo isotopes." Physical Review C 73.4 (2006): 044308. (Year: 2006).*
Y Dannon et al. "Production of Mo-99 Using 30 MeV Electrons and a Mo-100 Target", Reactor and Accelerator-Based Production of Mo-99-II, pp. 1081-1082.
Darleane Christian et al., "Preparation of Co by a (y,n) Reaction", Letters to the Editor, Oct. 25, 1950, Institute for Atomic Research.

* cited by examiner

PRODUCTION OF RADIOISOTOPES

CROSS-REFERENCE TO RELATED APPLICATIONS

This application is a National Stage of International Application No. PCT/IB2018/054858, filed Jun. 29, 2018, claiming the priority of ZA 2017/04408, filed on Jun. 29, 2017, the content of each of which is incorporated by reference herein.

FIELD OF THE INVENTION

THIS INVENTION relates to the production of radioisotopes. The invention provides for obtaining or producing, from a target compound, a radioisotope of a target element comprised in the target compound.

BACKGROUND TO THE INVENTION

IN THE FIELD OF RADIONUCLIDE THERAPY, or radiopharmaceuticals, which is distinct from radiotherapy, the global medical industry relies on a limited number of commercial scale suppliers of radioisotopes.

Radiopharmaceuticals are pharmaceuticals that are most often administered intravenously. They are not devices and therefore fall under the EMA and FDA regulations for pharmaceuticals. Their action is not through the chemical vector that accompanies (commonly referred to as radiolabelling) but rather through the radioactivity of the radioisotope included in such pharmaceutical preparations.

The characteristic of the radioisotope indicates whether a radiopharmaceutical is an imaging or a therapeutic agent. Gamma and Beta-plus emitters are used for imaging while Beta-minus, Alpha and Auger are used for internal radiotherapy.

The latter is the main difference between external beam radiotherapy, where the beam is directed from outside the patient to radiate certain areas/organs inside the body, and internal radiotherapy (which is achieved through the use of radiopharmaceuticals), where the radiation comes from radioisotopes that are carried to the correct organ via a vector and the radiation is delivered locally.

For imaging the difference is similar, i.e. radiation from outside the body (e.g. X-ray and CT scans) versus radiation from inside the body (radiopharmaceuticals).

It would be advantageous for medical treatment facilities that offer radionuclide therapy, to be able to become producers of radionuclides themselves. Currently, there are no viable options available to medical treatment facilities in this regard, taking into account that production of radioisotopes typically require equipment not readily available, or the presence of which is not readily permissible, in medical treatment facilities.

The present invention seeks to address the abovementioned situation.

SUMMARY OF THE INVENTION

IN ACCORDANCE WITH A FIRST ASPECT OF THE INVENTION, IS PROVIDED a method of obtaining or producing, from a target compound, a radioisotope of a target element comprised in the target compound, the method including irradiating the target compound with high energy photon irradiation (or gamma irradiation) and thereby forming the target element radioisotope, wherein the target element radioisotope is of different oxidation state than the target element and is comprised in a target element radioisotope compound that is separable from the target compound by a physical and/or chemical separation method.

The target element is therefore selected such that irradiation thereof with high energy photon irradiation causes a change in the oxidation state of the target element and forms the target element radioisotope, comprised in the target element radioisotope compound.

It will be appreciated that the terms "radioisotope(s) of the target element" and "target element radioisotopes" are used interchangeably and therefore have the same meaning. It should in this regard be appreciated that a "radioisotope" is a radioactive isotope of the target element. It is not a "normal" or "stable" (in the sense of radioactivity) isotope. It may be that in performing the method of the invention some "normal" or "stable" (in the sense of radioactivity) isotopes of the same oxidation state as the target element radioisotope would form, due to isotopic exchange.

Furthermore, it must be noted that the use of the term "radioisotope" in this specification means a particular radioisotope species and that, in fact, multiple radioisotopes of a particular radioisotope species would be formed in performing the method. The invention also does not exclude a possibility to produce multiple radioisotope species simultaneously, e.g. by irradiating more than one target element simultaneously. For the purposes of the specification, references to "radioisotope" therefore mean "at least one" radioisotope species, and may therefore include multiple different radioisotope species, and references to "radioisotopes" means multiple radioisotopes of that at least one species, and may therefore include multiple radioisotopes of multiple radioisotope species.

In addition, it must be noted that the term "element" as used in this specification is used in the chemical sense, with reference to elements as listed in the Periodic Table of Elements, unless the context clearly indicates otherwise.

It must also be noted that the target compound may consist exclusively of the target element, and thus the concept "target compound" includes elemental forms, e.g. elemental gases, liquids or solids, of the target element, which would not necessarily be in the form of a compound in the strict sense of the word. This also applies to the target element radioisotope compound, which may also consist exclusively of the target element radioisotope and would therefore also not necessarily be in the form of a compound in the strict sense of the word. Thus, the meaning of "compound" as used in this specification is not limited to the ordinary dictionary meaning thereof, although that meaning is included.

The target element radioisotope compound therefore is a compound that contains or includes, or that is the radioisotope of the target element that would be obtained or produced, in accordance with the method of the invention. In other words, in accordance with the definition afforded to "compound" in this specification, the target element radioisotope compound may either be a compound in the strict sense of the word, i.e. comprising the target element radioisotope in combination with another chemical species (e.g. as an oxide, or other as described below), or comprising the target element radioisotope in elemental form.

It should, still further, be noted that nothing in this specification should be understood as requiring complete conversion of all of the target element that is irradiated with the high energy photon irradiation, to the target element radioisotope.

It must also be noted that "high energy photon irradiation" is to be understood, as it would be understood by persons skilled in the art, to be gamma irradiation. It includes all electromagnetic waves (photons) with an energy higher than 100 keV. \

In this sense "irradiation" is, of course, of the target compound, with the "irradiation" being provided by "radiation," i.e. high energy photon, or gamma, radiation. It is therefore the high energy photon, or gamma, radiation that irradiates the target compound.

It is useful at this point to distinguish between high energy photon radiation or gamma radiation and so-called X-rays. An X-ray is a type of electromagnetic radiation, and its wavelength ranges from 0.01 to 10 nanometers, which places its frequencies in the 30 petahertz to 30 exahertz range. This means that X-rays have shorter wavelengths than UV rays and longer wavelengths than gamma rays (see below).

Gamma rays are also comprised of electromagnetic radiation of high frequencies, and are produced through the interaction of sub-atomic particles via electron-positron annihilation, fusion, and fission among other processes. Gamma rays generally have frequencies higher than 1019 Hz, and their energies are measured as higher than 100 keV, with wavelengths less than 10 picometers, which makes them smaller than atoms.

Gamma rays that result from radioactive decay have energies that are measured at a few hundred keV, and they are generally less than 10 MeV. While there is no lower limit to such energies, the upper limit has been pegged at approximately 20 MeV. High energy photons are not produced from radioactive decay (main difference with gamma rays from radioactive decay) and can range from 100 keV to 50 MeV or higher.

In accordance with the invention, the formation of the target element radioisotope result from a so-called γ (gamma), n reaction, due to the irradiation of the target compound with the high energy photon, or gamma, irradiation. For example, in one exemplary embodiment of the invention in which production of molybdenum-99, as target element radioisotope, is desired from molybdenum-100, as target element, the reaction would be Mo-100 (γ,n) Mo-99. It should be noted again that the radioactive isotope Mo-99 (i.e. the radioisotope Mo-99) is referred to here, not the "normal" or "stable" (in the sense of radioactivity) isotope. As a typical, preferred, embodiment of the invention, the occurrence of an γ,n reaction is required. Thus, the target element is required to be selected such that irradiation thereof with the gamma irradiation would result in a γ,n reaction taking place that produces the target element radioisotope.

For the target element radioisotope compound to be a compound in the strict sense of the word, the irradiation of the target element may take place in the presence of an additional reactant, that would cause formation of the target element radioisotope compound. The additional reagent may, for example, be an oxidising agent, such as oxygen or a halogen. The additional reactant may, for example, required to form the target element radioisotope in a particular desired material form, i.e. solid, liquid or gas, as the target element radioisotope compound. For example, if the target element compound is $Mo(CO)_6$ as exemplified below, the irradiation of the $Mo(CO)_6$ may be effected in the presence of oxygen, such that the $^{99}Mo$ that is formed by the γ,n reaction forms as solid $MoO_3$, as also hereinafter described.

The above, i.e. the requirement for an additional reactant for the target element radioisotope compound to be a compound in the strict sense of the word is not an absolute requirement however. It is possible that the target compound, when it is a compound in the strict sense of the word, would undergo an internal rearrangement and that the target element radioisotope compound would thus be formed into a particular desired material form without the requirement for or involvement of an additional reactant, whether such a material form is the same as the material form of the target compound, or not. In this regard it is noted that, in accordance with the invention as herein described, the target compound and the target element radioisotope compound may be in the same state of matter. Where the state of matter is a solid, both may be contained in the same "piece" or "body" of material that previously comprised only of the target compound, when such a piece of material was subjected to the irradiation. Of course solid forms of the target compound are not limited to singular pieces of material and other forms such as granular forms may be used.

The target element may be selected from alkali metals, alkali-earth metals, transition metals, post-transition metals, metalloids, polyatomic non-metals, diatomic non-metals, lanthanide series elements, and actinide series elements.

More specifically, the target element may be selected from one or combinations of two or more of Mo, Rb, Re, Sm, Y, Sr, In, Gd, Ac, Bi, Cu, Au, Pt, Sn, Pd, Rh, Lu, Ra, Th, P, I, Pb, Tl, Sb, Co, Ho, Sc, Tc, Ga, Fe, Zn, Ti, Zr, F, Nd, Pr, Tb. In one exemplary embodiment of the invention, as alluded to above, in which the target element is molybdenum, the target element may, in particular, be molybdenum-100 ($^{100}Mo$).

The target compound, when it is a compound in the strict sense of the word, may be selected from one or combinations of two or more of carbonates, halides, sulphates, oxide, oxalates, hydroxides and nitrates of the target element. As will be appreciated from the definition of "compound" supplied above, however, the target compound is not limited to such forms of the target element. Other forms, and specifically elemental forms, are included.

In the exemplary embodiment of the invention of the target element being molybdenum, and more particularly molybdenum-100, the target compound may, for example, be molybdenum hexacarbonyl ($Mo(CO)_6$).

Preferably, the target compound is in gaseous form. In the exemplary embodiment of the invention of the target compound being $Mo(CO)_6$, in particular, the $Mo(CO)_6$ may be gaseous $Mo(CO)_6$. The target compound may, however, in some embodiments of the invention alternatively or additionally be in solid form and/or in liquid form.

The target element radioisotope may be selected from one or combinations of two or more of $^{99}Mo$, $^{82}Rb$, $^{188}Re$, $^{186}Re$, $^{153}Sm$, $^{16}Ho$, $^{90}Y$, $^{89}Sr$, $^{111}In$, $^{153}Gd$, $^{225}Ac$, $^{212}Bi$, $^{213}Bi$, $^{211}At$, $^{60}Cu$, $^{61}Cu$, $^{67}Cu$, $^{64}Cu$, $^{62}Cu$, $^{198}Au$, $^{199}Au$, $^{195m}Pt$, $^{193m}Pt$, $^{197}Pt$, $^{117m}Sn$, $^{103}Pd$, $^{103m}Rh$, $^{177}Lu$, $^{223}Ra$, $^{224}Ra$, $^{227}Th$, $^{32}P$, $^{161}Tb$, $^{33}P$, $^{203}Pb$, $^{201}Tl$, $^{119}Sb$, $^{58m}Co$, $^{161}Ho$, $^{44}Sc$, $^{99m}Tc$, $^{67}Ga$, $^{68}Ga$, $^{59}Fe$, $^{63}Zn$, $^{52}Fe$, $^{45}Tl$, $^{191m}Pt$, $^{89}Zr$, $^{18}F$, $^{131,125,124,123}I$, $^{140}Nd/Pr$, and $^{155,156}Tb$.

In the exemplary embodiment of the invention of molybdenum, and more particularly molybdenum-100, being the target element, the target element radioisotope may, for example, be molybdenum-99 ($^{99}Mo$).

The target element radioisotope compound, when it is a compound in the strict sense of the word, may be selected from one or combinations of two or more of carbonates, halides, sulphates, oxides, oxalates, hydroxides and nitrates of the target element radioisotope. As will be appreciated from the definition of "compound" supplied above, however, the target element radioisotope compound is not limited to such forms of the target element radioisotope. Other forms, and specifically elemental forms, are included.

In the exemplary embodiment of the invention of molybdenum, and more particularly molybdenum-100, being the target element, the target element radioisotope compound may, particularly in the exemplary case of molybdenum-99 ($^{99}$Mo) being the target element radioisotope, for example be molybdenum trioxide ($MoO_3$).

In the exemplary embodiment of the invention of the target compound being $Mo(CO)_6$ and the target element radioisotope compound being $MoO_3$, as hereinbefore described, it would be appreciated that the oxidation state of molybdenum-100 in the $Mo(CO)_6$ and the oxidation state of molybdenum-99 ($^{99}$Mo) in the $MoO_3$, are different as required in accordance with the invention.

Preferably, the target element radioisotope compound is in solid form. It may, however, in some embodiments of the invention additionally or alternatively be in gaseous form and/or in liquid form. Thus, the target element radioisotope compound may be in the same physical form as the target compound, or it may be in a different physical form. In the case of $MoO_3$, the $MoO_3$ would typically be in solid form.

In any event, in one embodiment of the invention it is preferred that the state of matter of the target element radioisotope compound is different to the state of matter of the target compound. In other words, if the target compound is in gaseous form, the method would be carried out such that the target element radioisotope compound would be in solid form or, less typically, in liquid form. It will be appreciated that such a difference in state would allow for separation of the target element radioisotope compound from the target compound by means of a physical separation method.

In a case in which the state of matter of the target element radioisotope compound and the state of matter of the target compound are the same, the two would typically need to be separated by a chemical separation method.

The method may, in one embodiment of the invention, be carried out such that the target element radioisotope compound precipitates in solid form onto a solid surface, e.g. a solid surface of a chamber containing the target compound in gaseous form, when the target compound in gaseous form is irradiated with the high energy photon irradiation (gamma irradiation). It would be appreciated that this approach is well suited to the exemplary embodiment of the invention described hereinbefore, of the target compound being $Mo(CO)_6$ in gaseous form and the target element radioisotope compound being $MoO_3$, in solid form, as also hereinbefore described.

In one convenient, and advantageous, embodiment of the invention, the high energy photon irradiation (or gamma irradiation) may be that produced by a radiation therapy device, as used in medical radiation therapy. An example of such a device is a linear particle accelerator (Linac) that forms the source of radiation in an IMRT (Intensity Modulated Radiotherapy) machine used to irradiate/treat patients.

Alternatively, the high energy photon irradiation (gamma irradiation) may be produced by gamma decay of a gamma radiation source element or compound, by subjecting the gamma radiation source element or compound to electron beam irradiation. The high energy photon irradiation (or gamma irradiation) may therefore be produced by interaction of the electron beam with the gamma radiation source element or compound.

Typically, the gamma radiation source element or compound would be in solid form, but it may be in liquid form or gaseous form instead, or in a combination thereof.

The gamma radiation source element or compound may be provided, and thus may be subjected to electron beam irradiation, separately of the target compound, to produce the required high energy photon irradiation (or gamma irradiation). In such a case, the gamma radiation produced due to gamma decay of the gamma radiation source element or compound may be directed to irradiate the target compound, i.e. directed from its place of origin to irradiate the target compound. It may, however, be that the gamma radiation source element or compound may be provided separately of, but in irradiating proximity to the target compound in which case directing the gamma radiation to irradiate the target compound would not necessarily be required.

Alternatively, the gamma radiation source element or compound may be provided, and thus may be subjected to electron beam irradiation, jointly with the target compound, i.e. while the gamma radiation source element or compound is physically in the presence of the target compound and with the target compound thus effectively being subjected to electron beam irradiation as well, such that the gamma radiation is produced and gamma irradiation of the target compound is effected while the gamma radiation source element is physically in the presence of the target compound.

Conveniently, and advantageously, the electron beam irradiation may be provided by an electron beam which may be that of a radiation therapy device, as used in medical radiation therapy. An example of such a device is a linear particle accelerator (Linac) that forms the source of radiation in an IMRT (Intensity Modulated Radiotherapy) machine used to irradiate/treat patients.

Thus, the required gamma radiation may be that which is conventionally produced by a radiation therapy device, with which the target compound is then directly irradiated, or the required gamma radiation may be obtained by placing the target compound, including the gamma radiation source element or compound separately or physically in the presence of the target compound, in the path of an electron beam produced by a radiation therapy device.

Thus, radioisotopes of the target element are obtained from the target compound, the radioisotopes being comprised in the target element radioisotope compound.

The method may include recovering the target element radioisotope compound by separating it by physical or chemical techniques from the target compound.

IN ACCORDANCE WITH A SECOND ASPECT OF THE INVENTION, IS PROVIDED use of an of a radiation therapy device in obtaining radioisotopes of a target element in accordance with the method of the first aspect of the invention.

In one embodiment of the invention, the use may include placing the target compound in the path of gamma radiation produced by the radiation therapy device and irradiating the target compound with the gamma radiation.

In another embodiment of the invention, the use may include placing a gamma radiation source element or compound in the path of an electron beam produced by the radiation therapy device thereby to cause the gamma radiation source element or compound to produce gamma radiation, and may further include irradiating the target compound with the gamma radiation thus produced.

IN ACCORDANCE WITH A THIRD ASPECT OF THE INVENTION, IS PROVIDED a module for using a radiation therapy device in accordance with the second aspect of the invention, the module comprising a chamber configured to contain a target compound comprising a target element and, optionally, a gamma radiation source element or compound physically in the presence of the target compound or separately of the target compound, wherein the module is configured to be operatively received by the radiation therapy device
to locate the target compound in the path of gamma radiation produced by the device in use, or
to locate the gamma radiation source element or compound in the path of an electron beam produced by the device in use, wherein the gamma radiation source element or compound is then in irradiating proximity to the target compound.

IN ACCORDANCE WITH A FOURTH ASPECT OF THE INVENTION IS PROVIDED a radiation therapy device configured operatively to receive a module in accordance with the third aspect of the invention such that
the target compound is located in the path of gamma radiation produced by the device in use, or
the gamma radiation source element or compound is located in the path of an electron beam produced by the device in use.

IN ACCORDANCE WITH A FIFTH ASPECT OF THE INVENTION IS PROVIDED a radiation therapy device assembly comprising the radiation therapy device of the fourth aspect of the invention and the module of the third aspect of the invention operatively received by the radiation therapy device.

IN ACCORDANCE WITH A SIXTH ASPECT OF THE INVENTION IS PROVIDED a medical treatment facility that includes the radiation treatment device in accordance with the fourth aspect of the invention or the radiation treatment device assembly in accordance with the fifth aspect of the invention.

IN ACCORDANCE WITH A SEVENTH ASPECT OF THE INVENTION IS PROVIDED a method of using a radiation therapy device to obtain radioisotopes of a target element comprised in a target compound, the method including locating the target compound in the path of gamma radiation produced by the device in use.

IN ACCORDANCE WITH AN EIGHT ASPECT OF THE INVENTION IS PROVIDED a method of using a radiation therapy device to obtain radioisotopes of a target element comprised in a target compound, the method including locating a gamma radiation source element or compound, which is in irradiating proximity to the target compound, in the path of an electron beam produced by the device in use.

IN ACCORDANCE WITH A NINTH ASPECT OF THE INVENTION, IS PROVIDED an arrangement of parts for obtaining radioisotopes of a target element comprised in a target compound, the arrangement including
a gamma radiation generator, that produces gamma radiation in use; and
the target compound contained in a chamber and located in the path of gamma radiation produced by the gamma radiation generator in use.

IN ACCORDANCE WITH A TENTH ASPECT OF THE INVENTION, IS PROVIDED an arrangement of parts for obtaining radioisotopes of a target element comprised in a target compound, the arrangement including
an electron beam generator;
a gamma radiation source element or compound located in the path of the electron beam produced by the electron beam generator in use; and
the target compound contained in a chamber and located in irradiating proximity to the gamma radiation source element or compound, so as to be irradiated with gamma irradiation emitted from the gamma radiation source element or compound in use.

The gamma radiation source element or compound may be in solid form.

The target compound may be in gaseous form.

The target compound and the gamma radiation source element or compound may be in each other's physical presence, or they may be separate of each other.

DETAILED DESCRIPTION OF EXEMPLARY EMBODIMENTS OF THE INVENTION

Figure 2:
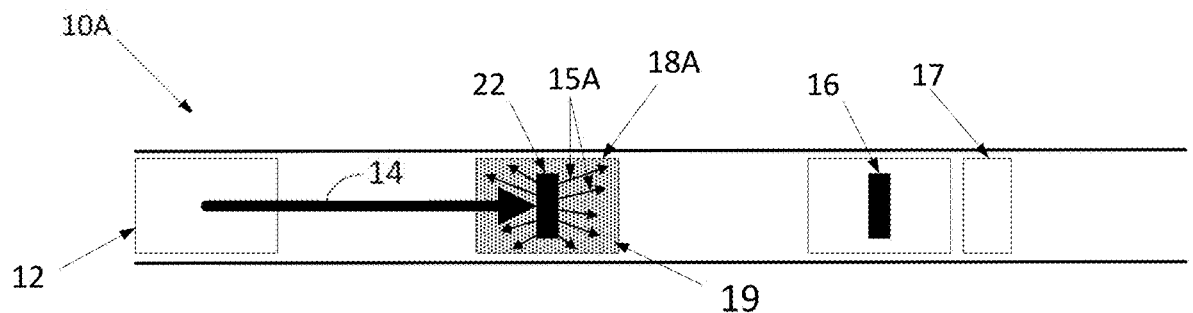

THE INVENTION WILL NOW BE DESCRIBED IN MORE DETAIL, with reference to the following drawings in which FIG. 1 shows, diagrammatically, operative parts of one embodiment of a radiation therapy device assembly in accordance with the invention; and FIG. 2 shows, diagrammatically, operative parts of another embodiment of a radiation therapy device assembly in accordance with the invention.

Referring to the drawings, and in particular to FIG. 1, reference numeral 10 generally indicates operative parts of one embodiment of a radiation therapy device assembly in accordance with the invention, for performing one embodiment of the method of the invention.

The parts 10 comprise an electron beam generator 12 which emits, in use, an electron beam 14. The parts 10 also comprise a gamma radiation generation target 16 in the form of a gamma radiation source element, e.g. tungsten.

The gamma radiation generation target 16 is provided in the path of the electron beam 14 in use.

The parts 10 also comprise a module 18 in accordance with the invention, which module 18 contains a target compound 19, e.g. $Mo(CO)_6$, in gaseous form, which target compound comprises a target element, e.g. $^{100}Mo$, of which a target element radioisotope, e.g. $^{99}Mo$, is desired, in the form of a target element radioisotope compound, e.g. $MoO_3$. The module may comprise a further reactant, e.g. oxygen, to render the target element radioisotope into a particular desired material form that it does not achieve merely due to the high energy photon irradiation of the target compound. As explained above it is possible, however, that the high energy photon irradiation would be sufficient for the target element radioisotope to form as the target element radioisotope compound in a particular desired material form, without the involvement of an additional reactant. To contain the target compound 19, the module 18 defines a target compound chamber in which the target compound can be contained.

It will be appreciated from the drawing that the module 18 is effectively located "downstream" of the gamma radiation generation target 16, with reference to the direction in which the electron beam 14 is in use emitted.

In use, in performing one embodiment of the method of the invention, the electron beam 14 emitted from the electron beam generator 12 hits the gamma radiation generation target 16, from which gamma radiation 15 is then emitted as a result of irradiation thereof with the electron beam 14. Some of the gamma radiation 15 is directed by a collimator 17 into directed gamma radiation 20. The directed gamma radiation 20, which is conventionally for use in radiation therapy, irradiates the module 18, and therefore also the target compound 19. This converts, through a γ,n reaction and the Szilard-Chalmers effect, the target element, e.g. $^{100}Mo$, to the target element radioisotope, e.g. $^{99}Mo$, which precipitates inside the module 18 in solid form as the target element radioisotope compound, e.g. MoO₃, due to the reaction thereof with the oxygen, thus obtaining isotopes of the target element.

Referring to FIG. 2, reference numeral 10A shows another embodiment of parts of a radiation therapy device according to the invention.

Some of the parts of the radiation therapy device illustrated in FIG. 2 are identical to those of the parts of the radiation therapy device illustrated in FIG. 1, and the same reference numerals are used in respect of such parts in FIG. 2.

Differences between the parts of the radiation therapy device of FIG. 1 and the parts of the radiation therapy device of FIG. 2 include the configuration of the module 18, which is therefore referenced in FIG. 2 by reference numeral 18A, and the location of the module 18A.

With respect to location, the module 18A is located "upstream" of the gamma radiation generation target 16, and therefore not in the path of the gamma radiation 20. Instead, the module 18A is located in the path of the electron beam 14.

With respect to configuration, the module 18A includes a gamma radiation source element or compound 22. Such gamma radiation source element or compound is therefore provided in the device 10A in addition to the gamma radiation generation target 16. In this regard, the module 18A is configured such that the gamma radiation source element or compound 22 is physically in the presence of, or is at least in irradiating proximity to, the target compound 19.

In use, in performing another embodiment of the method of the invention, the device 10A would conventionally operate in the same manner as the device 10 to produce the directed gamma radiation 20 that is, again, conventionally for use in radiation therapy. In the context of the invention, in contrast to the device 10, however, radioisotopes of the target element of the target compound 19 are not obtained by irradiation of the target compound with the gamma radiation 20, since such (therapeutic) gamma radiation would not be produced by the device 10A in the configuration illustrated in FIG. 2, but with gamma radiation 15A emitted from the gamma radiation source element or compound 22. As in the case of the embodiment 10 illustrated in FIG. 1, this converts, through a γ,n reaction and the Szilard-Chalmers effect, the target element, e.g. $^{100}$Mo, to the target element radioisotope, e.g. $^{99}$Mo, which precipitates inside the module 18 in solid form as the target element radioisotope compound, e.g. MgO₃, due to the reaction thereof with the oxygen, thus obtaining isotopes of the target element.

CONCLUSION

IT IS BELIEVED that the invention as described herein would allow for medical treatment facilities to produce, without major overhaul of equipment or infrastructure, radioisotopes in-house. The advantage of this possibility is clear.

The invention claimed is:

1. A method of producing a radioisotope of a target element ("target element radioisotope"), the method including:
   irradiating a target compound, comprising the target element, with gamma radiation, as high energy photon irradiation, in a radiation therapy device, wherein the irradiation is performed upstream of a gamma radiation generation target of the radiation therapy device and wherein the gamma radiation is produced as high energy photon irradiation by irradiating a gamma radiation source element or compound with electron beam radiation of an electron beam that is produced by the radiation therapy device, thereby producing the target element radioisotope,
   wherein the target element radioisotope is a radioisotope of the target element and is of an oxidation state different than that of the target element and is comprised in a target element radioisotope compound that is different from the target compound and that is separable from the target compound by a physical and/or chemical separation method; and
   wherein the target compound is in gaseous form and is contained in a target compound chamber defined by a module of the radiation therapy device, which module is located in the path of the electron beam upstream of the gamma radiation generation target of the radiation therapy device, and which module contains, in addition to the target compound, the gamma radiation source element or compound.

2. The method according to claim 1, wherein the target element is selected from alkali metals, alkali-earth metals, transition metals, post-transition metals, metalloids, polyatomic non-metals, diatomic non-metals, lanthanide series elements, and actinide series elements.

3. The method according to claim 1, wherein the target element is selected from one or combinations of two or more of Mo, Rb, Re, Sm, Y, Sr, In, Gd, Ac, Bi, Cu, Au, Pt, Sn, Pd, Rh, Lu, Ra, Th, P, I, Pb, Tl, Sb, Co, Ho, Sc, Tc, Ga, Fe, Zn, Ti, Zr, F, Nd, Pr, Tb.

4. The method according to claim 1, wherein the target compound is selected from one, or combinations of two or more of carbonates, halides, sulphates, oxides, oxalates, hydroxides and nitrates of the target element.

5. The method according to claim 1, wherein the target compound is an elemental form of the target element.

6. The method according to claim 1, wherein the target element radioisotope is selected from one, or combinations of two or more of $^{99}$Mo, $^{82}$Rb $^{188}$Re, $^{186}$Re, $^{153}$Sm, $^{166}$Ho, $^{90}$Y, $^{89}$Sr, $^{111}$In, $^{153}$Gd, $^{225}$Ac, $^{212}$Bi, $^{213}$Bi, $^{211}$At, $^{60}$Cu, $^{61}$Cu, $^{67}$Cu, $^{64}$Cu, $^{62}$Cu, $^{198}$Au, $^{199}$Au, $^{195m}$Pt, $^{193m}$Pt, $^{197}$Pt, $^{117m}$Sn, $^{103}$Pd, $^{103m}$Rh, $^{177}$Lu, $^{223}$Ra, $^{224}$Ra, $^{227}$Th, $^{32}$P, $^{161}$Tb, $^{33}$P, $^{203}$Pb, $^{201}$Tl, $^{119}$Sb, $^{58m}$Co, $^{161}$Ho, $^{44}$Sc, $^{99m}$Tc, $^{67}$Ga, $^{68}$Ga, $^{59}$Fe, $^{63}$Zn, $^{52}$Fe, $^{45}$Tl, $^{191m}$Pt, $^{89}$Zr, $^{18}$F, $^{131,125,124,123}$I, $^{140}$Nd/Pr, and $^{155,156}$Tb.

7. The method according to claim 1, wherein the target element radioisotope compound is selected from one, or more combinations of two or more of carbonates, halides, sulphates, oxide, oxalates, hydroxides and nitrates of the target element radioisotope.

8. The method according to claim 1, wherein the state of matter of the target element radioisotope compound is different to the state of matter of the target element compound.

9. A method of producing a radioisotope of a target element ("target element radioisotope"), the method including:
   irradiating a target compound, comprising the target element, with gamma radiation, as high energy photon irradiation, in a radiation therapy device, wherein the irradiation is performed upstream of a gamma radiation generation target of the radiation therapy device and wherein the gamma radiation is produced as high energy photon irradiation by irradiating a gamma radiation source element or compound with electron beam radiation of an electron beam that is produced by the radiation therapy device, thereby producing the target element radioisotope, wherein the target element radioisotope is a radioisotope of the target element and is of an oxidation state different than that of the target element and is comprised in a target element radioisotope compound that is different from the target compound and that is separable from the target compound by a physical and/or chemical separation method; and wherein the target compound is in gaseous form and is contained in a target compound chamber defined by a module of the radiation therapy device, which module is located in the path of the electron beam upstream of the gamma radiation generation target of the radiation therapy device, and which module contains, in addition to the target compound, the gamma radiation source element or compound, wherein:

the target element is molybdenum-100 ($^{100}$Mo);

the target element is comprised by a target element compound that is molybdenum hexacarbonyl ($Mo(CO)_6$) in gaseous form;

the target element radioisotope is molybdenum-99 ($^{99}$Mo); and the target element radioisotope compound is molybdenum trioxide ($MoO_3$) in solid form, and the target element radioisotope compound is thus separable from the target element compound by a physical separation method.

\* \* \* \* \*